United States Patent [19]
Allred, III et al.

[11] Patent Number: 6,036,639
[45] Date of Patent: Mar. 14, 2000

[54] LARYNGOSCOPE HAVING LOW MAGNETIC SUSCEPTIBILITY AND METHOD OF ASSEMBLING

[75] Inventors: Jimmie B. Allred, III, Skaneateles; Earl R. Holdren, III, Auburn; Jack A. Belstadt, Lockport; Charles L. Mozeko, Tonawanda; Richard W. Mott, East Amherst; Jeffrey B. Mallon, Lockport; Philip S. Wutz, Williamsville; Michael F. Pyszczek, LeRoy, all of N.Y.

[73] Assignee: Minrad Inc., Buffalo, N.Y.

[21] Appl. No.: 08/837,339

[22] Filed: Apr. 11, 1997

[51] Int. Cl.$^7$ ..................................................... A61B 1/26
[52] U.S. Cl. ............................................ 600/193; 600/199
[58] Field of Search .................................. 600/184, 185, 600/199, 193

[56] References Cited

U.S. PATENT DOCUMENTS

| | | |
|---|---|---|
| 310,004 | 12/1884 | Weston . |
| 485,089 | 10/1892 | Carhart . |
| 1,067,646 | 7/1913 | Downey . |
| 1,877,077 | 9/1932 | Stevens . |
| 2,282,979 | 5/1942 | Murphy ........................................ 136/6 |
| 2,459,702 | 1/1949 | Hipwell et al. ...................... 240/10.66 |
| 2,651,763 | 9/1953 | Grimsley .................................... 339/93 |
| 2,864,880 | 12/1958 | Kaye ....................................... 136/111 |
| 2,982,807 | 5/1961 | Dassow et al. ......................... 136/173 |
| 3,352,715 | 11/1967 | Zaromb ..................................... 136/83 |
| 3,673,000 | 6/1972 | Ruetschi .................................. 136/107 |
| 3,890,498 | 6/1975 | Toth, Sr. .............................. 240/10.66 |
| 4,053,687 | 10/1977 | Coibion et al. ........................... 429/94 |
| 4,203,150 | 5/1980 | Shamlian ................................. 362/183 |
| 4,237,527 | 12/1980 | Breedlove ............................... 362/189 |
| 4,264,688 | 4/1981 | Catanzarite ............................. 429/163 |
| 4,273,112 | 6/1981 | Heine et al. ......................... 600/199 X |
| 4,286,311 | 8/1981 | Maglica ................................... 362/205 |
| 4,318,967 | 3/1982 | Ruetschi ................................... 429/48 |
| 4,406,280 | 9/1983 | Upsher .............................. 600/199 X |
| 4,595,641 | 6/1986 | Giurtino .................................... 429/1 |
| 4,596,239 | 6/1986 | Bauman ................................... 128/11 |
| 4,607,623 | 8/1986 | Bauman ................................... 128/11 |
| 4,613,926 | 9/1986 | Heitman et al. ......................... 362/32 |
| 4,824,298 | 4/1989 | Lippacher et al. ..................... 408/240 |
| 5,104,752 | 4/1992 | Baughman et al. ......................... 49/1 |
| 5,149,598 | 9/1992 | Sunshine ................................ 429/123 |
| 5,173,371 | 12/1992 | Huhndorff et al. ........................ 429/1 |
| 5,178,131 | 1/1993 | Upsher .............................. 600/199 X |
| 5,194,340 | 3/1993 | Kosako .................................... 429/1 |
| 5,316,323 | 5/1994 | Jovanovic ............................... 279/22 |
| 5,417,527 | 5/1995 | Wienhold ............................... 408/239 |
| 5,418,087 | 5/1995 | Klein ...................................... 429/101 |
| 5,443,924 | 8/1995 | Spellman ................................ 429/65 |
| 5,464,229 | 11/1995 | Salpaka ................................... 279/30 |
| 5,573,255 | 11/1996 | Salpaka ................................... 279/75 |
| 5,593,222 | 1/1997 | Maglica .................................. 362/157 |
| 5,601,359 | 2/1997 | Sharrah et al. ........................ 362/204 |

OTHER PUBLICATIONS

John Schneck of General Electric Corporate Research and Development Center, Schenectady, New York 12309, entitled "The Role of Magnetic Susceptibility in Magnetic Resonance Imaging: Magnetic Field Compatibility of the First and Second Kinds"; Dec. 9, 1993.

*Primary Examiner*—Jeffrey A. Smith
*Attorney, Agent, or Firm*—Hodgson Russ Andrews Woods & Goodyear LLP

[57] ABSTRACT

A laryngoscope constructed of materials including metal components having very low magnetic susceptibilities is described. The battery powering the laryngoscope lamp is a lithium battery also constructed of materials having low magnetic susceptibilities. The battery further includes a unique terminal configuration that prevents the inadvertent use of other batteries, including non-magnetic batteries, in the laryngoscope. A unique lamp retaining mechanism provides for quick and easy replacement of the lamp.

28 Claims, 5 Drawing Sheets

FIG. 3B

LARYNGOSCOPE HAVING LOW MAGNETIC SUSCEPTIBILITY AND METHOD OF ASSEMBLING

BACKGROUND OF THE INVENTION

1. Field of the Invention

The present invention generally relates to a hand held medical device. More particularly, the present invention relates to a laryngoscope, and still more particularly to a laryngoscope that is constructed of materials having relatively low magnetic susceptibilities. This provides the laryngoscope of the present invention as a useful instrument in the vicinity of a magnetic resonance scanner.

2. Prior Art

Laryngoscopes generally comprise a detachable blade and a cooperating handle which are connected together in an L-shaped configuration. The handle serves as an enclosure for one or more batteries which energize a light source in the handle. The switch for energizing the light source is usually positioned at the top of the handle immediately adjacent to the light source and is activated by the blade when it is connected to the handle and moved into an operative position. Light from the light source is directed to the light conductor disposed in or on the blade. Light passes through the light conductor to the distal end thereof to illuminate the field of view such as a patient's mouth and larynx during the examination thereof by medical personnel and during the insertion of an endotracheal tube into the trachea of the lungs to administer anesthetic gases therein.

The prior art is replete with various types of metallic laryngoscopes, some of which are capable of illumination. Additionally, U.S. Pat. No. 4,607,623 to Bauman describes a laryngoscope constructed of non-ferrous materials such as ABS with the electrically conductive portions provided by first applying a thin copper layer to the ABS followed by electroless plating and then electrolytically plating another copper layer to form a conductive layer about 0.5 to 2 mils thick. A thin layer of aluminum is subsequentially applied to the copper coating in those areas intended to be reflective. The batteries powering this device are not further described, but may be of a nickel/cadmium type commonly used for such application. Nickel/cadmium batteries are not considered to be relatively nonmagnetic and would not be useful with the laryngoscope of the present invention.

U.S. Pat. Nos. 310,004 to Weston; 485,089 to Carhart; 2,282,979 to Murphy; 3,352,715 to Zaromb; 3,673,000 to Ruetschi and 4,318,967 to Ruetschi disclose anti- or non-magnetic materials in cells or batteries. Additionally, U.S. Pat. Nos. 2,864,880 to Kaye; 2,982,807 to Dassow et al.; 4,053,687 to Coiboin et al.; 4,264,688 to Catanzarite; 4,595,641 to Giutino; 5,104,752 to Baughman et al.; 5,149,598 to Sunshine; 5,173,371 to Huhndorff et al.; 5,194,340 Kasako; 5,418,087 to Klein; and 5,443,924 to Spellman relate to batteries having means for assuring that proper battery polarity is established. However, none of these patents describe power sources that are useful with the hand held medical device of the present invention because they either include at least some magnetic components, do not have sufficient energy density for extended use or do not have a terminal configuration similar to that of the present invention. U.S. Pat. No. 4,613,926 to Heitman et al. discloses an illuminating assembly for an MRI scanner.

There is needed a lighted laryngoscope that is predominantly constructed of metal so that the instrument is capable of withstanding the abusive treatment conditions which surgical instruments are sometimes subjected to. For this purpose, the laryngoscope of the present invention is constructed largely of metal components. However, with ever increasing use of magnetic resonance scanning to aid medical personnel during pre- and post-clinical and surgical procedures, the metal components must be constructed of materials that have as low a magnetic susceptibility as possible.

SUMMARY OF THE INVENTION

The laryngoscope of the present invention is constructed of materials including metal components having very low magnetic susceptibilities. Those parts not made of metal are preferably formed of a thermoplastic material, for example an acetal compound such as DELRIN. The battery powering the laryngoscope lamp is also constructed of materials having low magnetic susceptibility. Lithium batteries are preferred, and all components such as the casing, terminal leads, current collectors and collector leads, some of which are typically made of nickel, are constructed of stainless steel nonmagnetic austenitic. The battery further includes a unique terminal configuration that prevents the inadvertent use of other batteries, including non-magnetic batteries, in the laryngoscope. A unique lamp retaining mechanism provides for quick and easy replacement of the lamp.

These and other aspects of the present invention will become more apparent to those skilled in the art by reference to the following description and to the appended drawings.

DETAILED DESCRIPTION OF THE INVENTION

Turning now to the drawings, FIGS. 1 to 7 show a laryngoscope 10 having low magnetic susceptibility characteristics according to the present invention and generally comprised of a handle 12, a detachable blade 14 and an attachment means 16 for detachably securing the blade 14 to the handle 12 in a generally L-shaped configuration. The instrument is utilized to depress a patient's larynx during an examination thereof or during the insertion of an endotracheal tube. The blade is of stainless steel or a fiberglass composite commercially available from Heine under the trademark SANALON.

Figure 1:
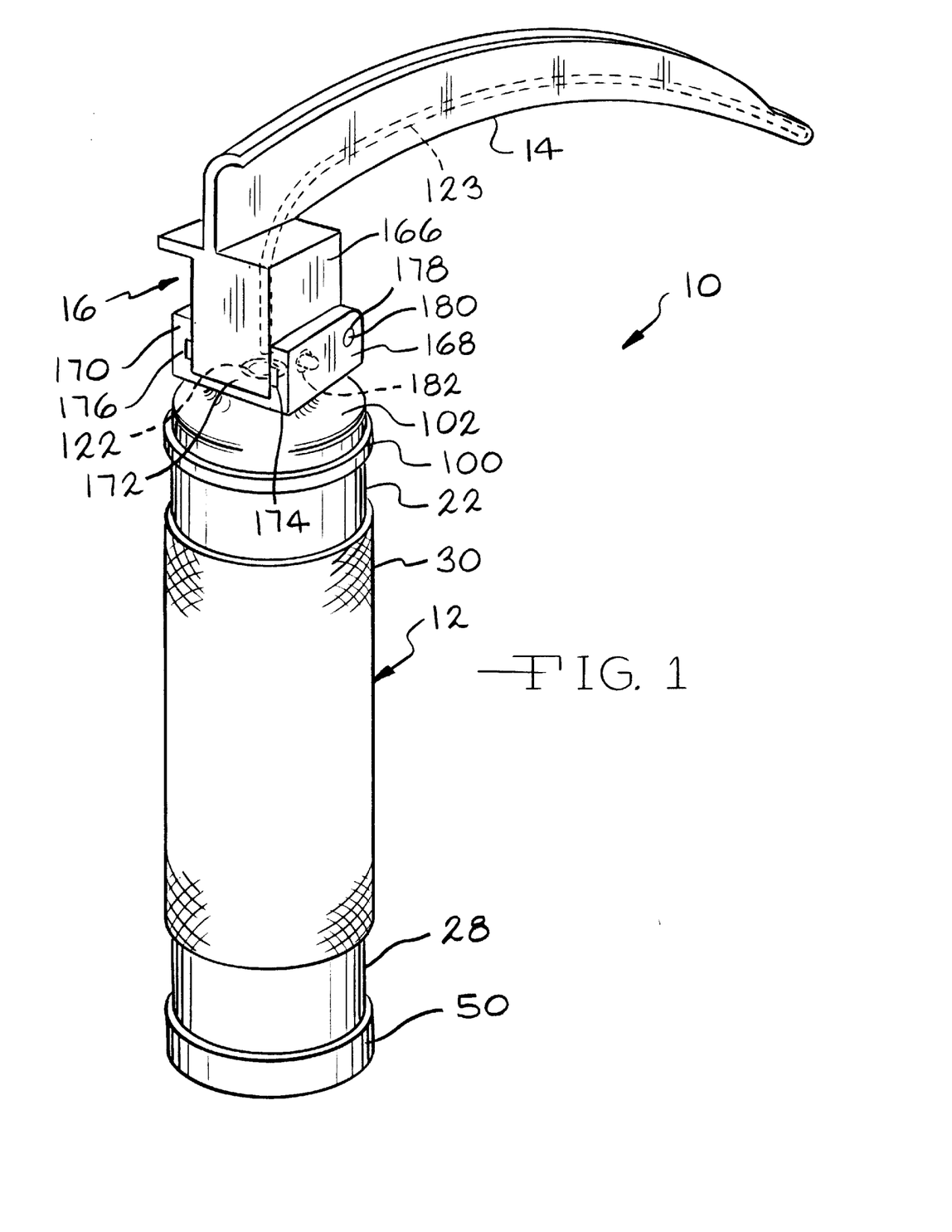
FIG. 1 is a perspective view of a laryngoscope 10 according to the present invention.
Figure 2:
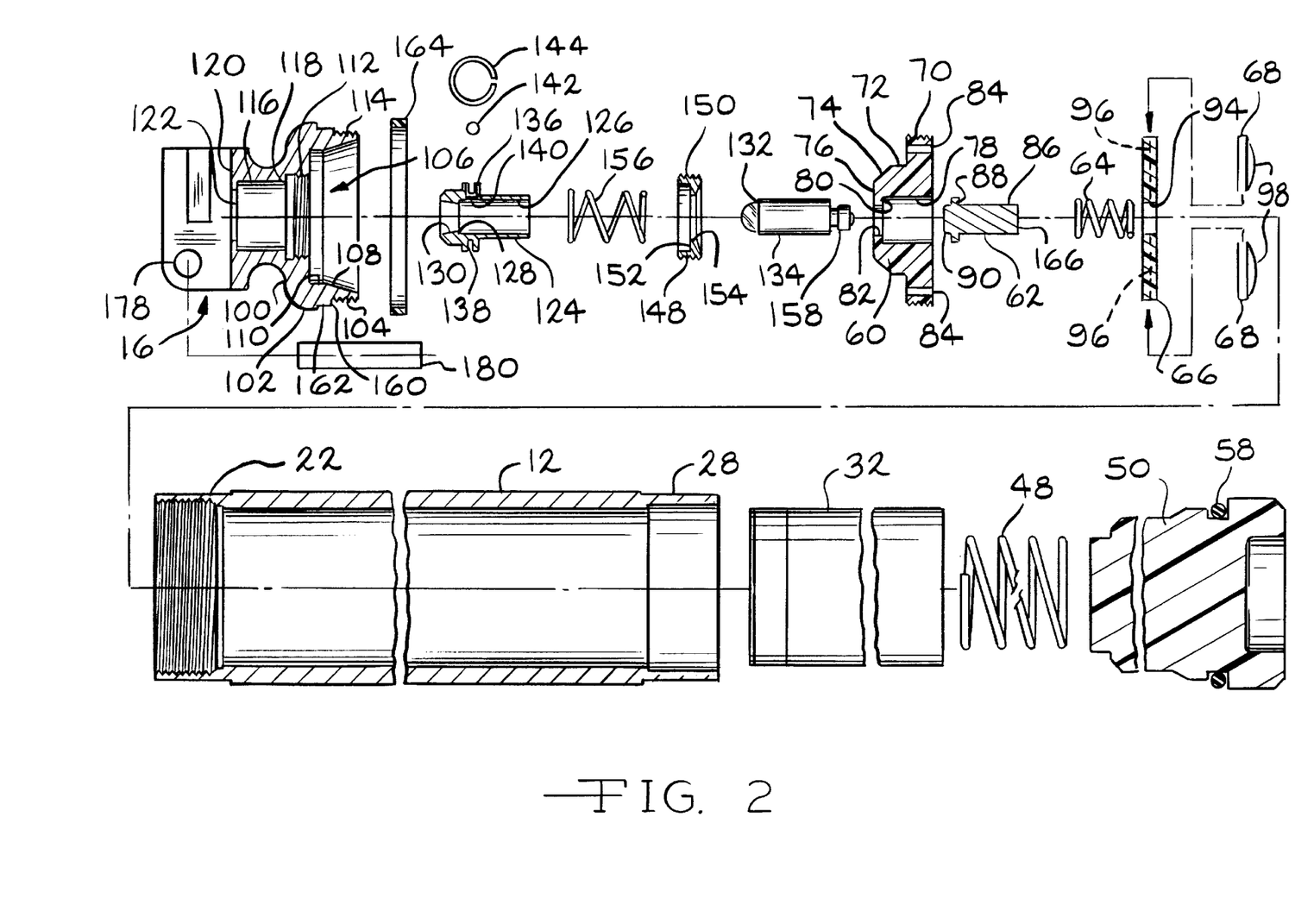
FIG. 2 is an exploded view of the laryngoscope handle 12 and head assembly.
Figure 3A:
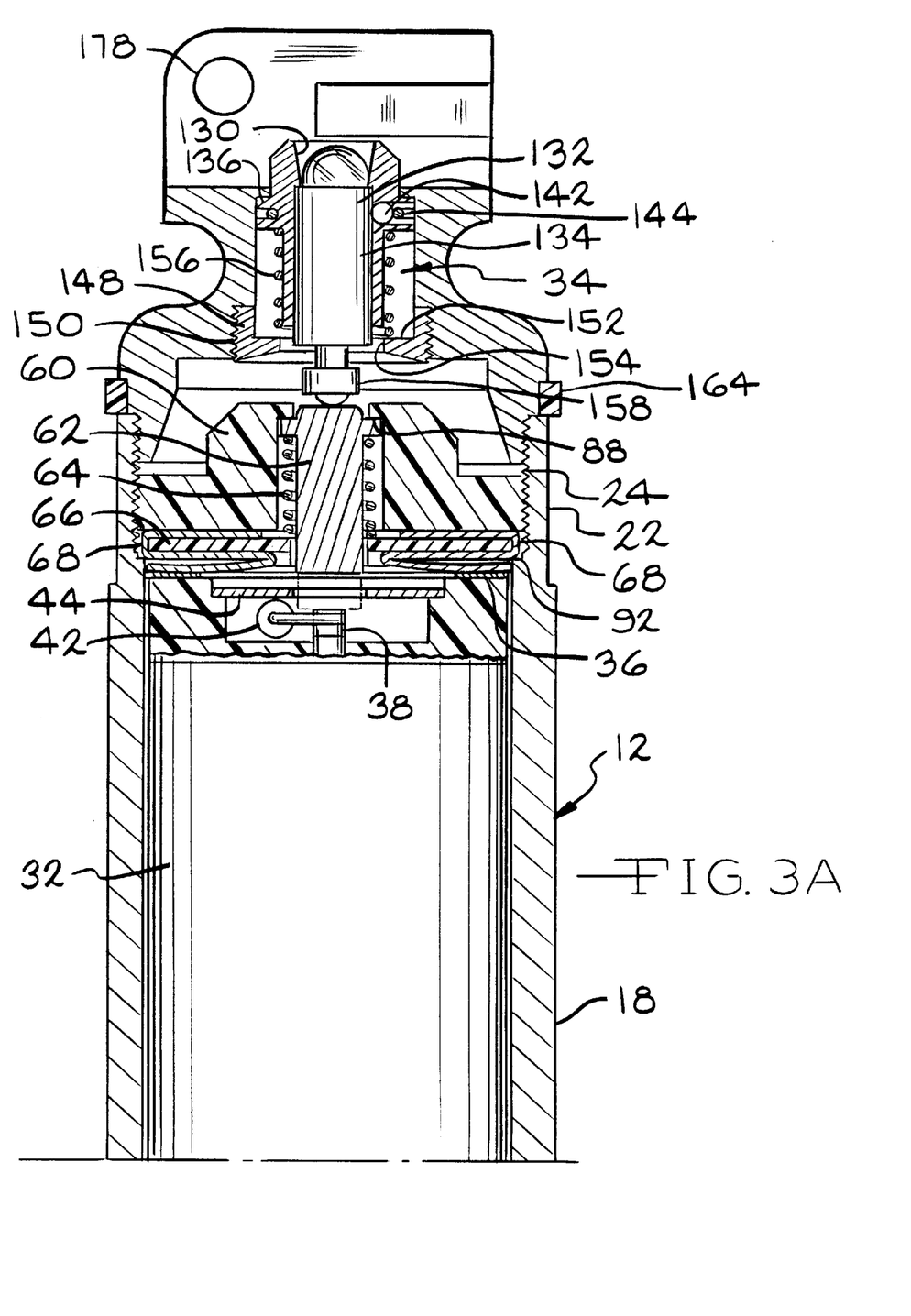
FIG. 3A is a partial, cross-sectional view of a portion of the handle 12 and the head assembly for the laryngoscope 10.
Figure 3B:
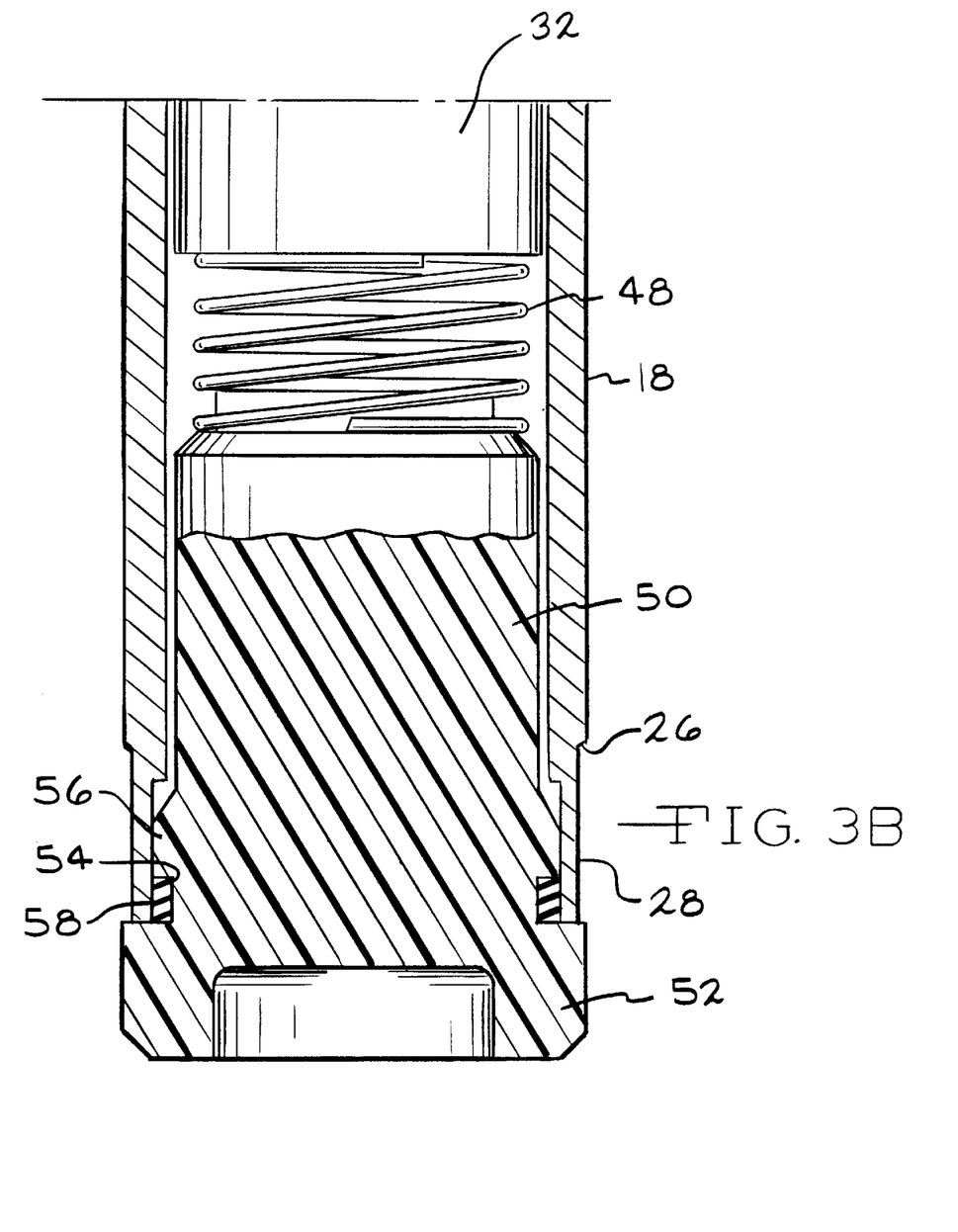
FIG. 3B is a partial, cross-sectional view of the handle 12 and end cap 50 for the laryngoscope 10.

With particular reference to FIGS. 2, 3A, and 3B, the handle 12 is a cylindrically-shaped tube comprising an intermediate section 18 meeting at a step 20 with a proximal section 22 having internal threads 24, and the intermediate section 18 meeting at a chamfer 26 with a distal section 28.

The outer surface of the handle 12 is provided with raised, knurled ridges 30 (FIG. 1) to aid in gripping the laryngoscope 10. The handle 12 is preferably constructed of chrome plated brass.

A battery 32 (FIGS. 2, 3A, 3B, 4 and 5) is housed inside the intermediate handle section 18 for providing power to a lamp means as an assembly 34, which will be described in detail hereinafter. The battery 32 is constructed of materials having relatively low magnetic susceptibility with a unique terminal configuration according to the present invention. The battery 32 is preferably an alkali metal battery and more preferably an alkali metal/liquid catholyte battery. A most preferred chemistry utilizes the lithium/thionyl chloride-bromine chloride (Li/BCX) couple. The battery casing adjacent to the distal handle section 28 is insulated to prevent electrical contact in the conventional manner.

Figure 4:
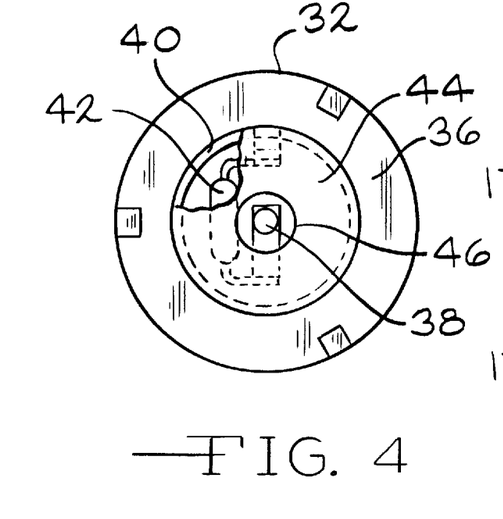
FIG. 4 is a plan view of the battery 32 for the laryngoscope 10.
Figure 5:
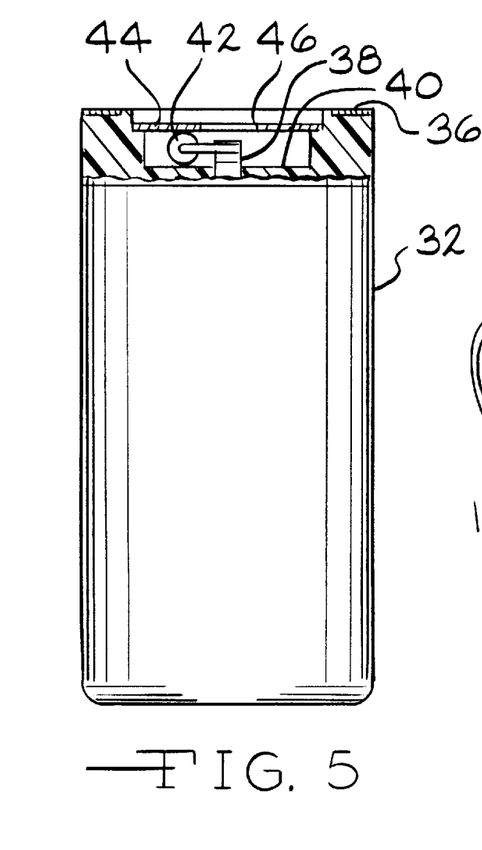
FIG. 5 is a side, elevational view of the battery 32.

As shown in FIGS. 3A, 4 and 5, the opposite end of the battery 32 includes a negative contact ring 36 that is permanently attached to the battery case to provide one terminal for the battery. The central, positive terminal 38 is recessed and insulated by material 40 around its perimeter to prevent accidental shortening. A non-magnetic fuse 42 prevents inadvertent run-away electrochemical reaction while a thermoplastic insulator plate 44 supported on a ledge of the insulated material 40 protects the positive terminal 38 and fuse 42. A central opening 46 in plate 44 provides for access to the positive terminal 38. To provide the battery 32 having a relatively low magnetic susceptibility, all external and internal electrical components such as the casing, the terminals 36,38, the current collectors and the contact leads are of stainless steel.

The unique terminal configuration prevents the inadvertent loading and discharge of batteries into the handle 12 not intended for use with the laryngoscope 10. Such inadvertent battery use could have detrimental affects on the laryngoscope's low magnetic susceptibility characteristics.

The battery 32 is secured inside the handle 12 by a cap spring 48, preferably of silver plated beryllium copper, that biases between the battery and an end cap 50 snug-fitted into the distal handle section 28 extending part way into the intermediate handle section 18. The end cap 50 is of a non-magnetic material, such as an acetal thermoplastic material with an enlarged head 52 that abuts the distal end of handle 12. A groove 54 formed between the cap head 52 and an annular protrusion 56 of the cap receives an O-ring 58 of a flexible elastomeric material for sealing the cap 50 in the distal section 28 of the handle 12 in a fluid tight engagement.

As shown in FIGS. 2 and 3A, a battery retainer assembly is threaded into the proximal handle section 22 and includes a battery retainer 60, preferably of an acetal thermoplastic material, that threads into the handle 12 to capture a battery pin 62, a battery spring 64, a tube disk 66 and a pair of spring contacts 68 therein. The battery pin 62 is preferably of gold plated brass, the battery spring 64 is preferably of silver plated beryllium copper, the tube disk 66 is of an acetal thermoplastic material and the spring contacts 68 are of silver plated beryllium copper.

The battery retainer 60 comprises a threaded portion 70 sized to threadingly mate with the internal threads 24 of the proximal handle section 22. The threaded portion 70 of the battery retainer 60 meets a cylindrically-shaped portion 72 that extends to a chamfer 74 ending at an end face 76. The battery retainer 60 has a first, cylindrically-shaped bore 78 that meets at an internal shoulder 80 with a second, lesser diameter cylindrically-shaped bore 82 extending to the end face 76. A pair of diametrically opposed openings 84 are provided through the thickness of the threaded portion 70. The battery retainer 60 receives the battery pin 62 having a cylindrically-shaped body 86 provided with an annular protrusion 88 adjacent to a proximal end 90 thereof.

The internal threads 24 at the proximal handle section 22 terminate at an internal shoulder 92. Shoulder 92 supports the tube disk 66 having a central opening 94. The tube disk 66 also includes a pair of opposed channels 96 (shown in dashed lines in FIG. 2) that communicate between the outer edge thereof and diametrically opposed portions of the opening 94. The tube disk 66 supports the pair of spring contacts 68, each having a leg disposed in one of the disk channels 96 with a contact portion 98 of the springs extending from the opposite face of the tube disk 66.

As shown in FIG. 3A, with the tube disk 66 supported on the internal shoulder 92, the spring contacts 68 are captured between the shoulder 92 and the disk 66 with the contact portions 98 contacting the annular, negative terminal 36 of battery 32. The tube disk 66 and spring contacts 68 are secured in this position by the battery retainer 60 threaded into the proximal handle section 22. The battery retainer 60 further captures the battery pin 62 between itself and the tube disk 66 with the proximal end side of the annular protrusion 88 abutted against the internal shoulder 80 of the battery retainer by the battery spring 64 surrounding the body 86 of the battery pin 62 and biasing between the tube disk 66 and the opposite side of the annular protrusion 88. The pair of diametrically opposed openings 84 in the battery retainer 60 are provided to receive a tool (not shown) such as a spanner wrench for tightening the battery retainer 60, battery pin 62, battery spring 64, tube disk 66 and spring contacts 68 into position. The battery retainer assembly together with the battery 32 loaded into the handle 12 and secured therein by the cap spring 48 and end cap 50 form the portion of the laryngoscope 10 of the present invention generally referred to as the battery pack assembly.

After the battery retainer assembly is threaded into the proximal handle section 22, the proximal section 22 threadingly receives a head 100. As shown in FIGS. 2, 3A, 4 and 6, the head 100 includes a cap portion 102 having external threads 104 that threadingly mate with the internal threads 24 at the proximal handle section 22, and the attachment means 16 for attaching the blade 14 to the handle 12. The head 100 is preferably constructed of chrome plated brass.

The head 100 further comprises an internal passage 106 extending from its threaded end through the cap portion 102 to the attachment means 16. At the threaded end, the bore 106 has a beveled portion 108 tapering inwardly toward a first cylindrical portion 110 that meets with an internally threaded portion 112 at step 114. The internal threaded portion 112 of head 100 meets with a second cylindrical portion 116 at step 118 which extends to a shoulder 120 that meets with an opening 122 (shown in dashed lines in FIG. 1) leading into the blade attachment means 16.

To provide illumination to a fiber optic blade light conductor 123 (shown in dashed lines in FIG. 1), the lamp assembly 34 is mounted in the internal bore 106 of head 100. The lamp assembly 34 includes a lamp retainer 124 (FIGS. 2, 3A and 7) having an interior cylindrically-shaped bore 126 extending to a shoulder 128 that meets with an outwardly beveled, reflector portion 130. The lamp retainer 124 is preferably constructed of stainless steel. A lamp 132 is received inside the bore 126 with the lamp casing 134 abutted against the shoulder 128 so that the lamp 132 is disposed in a reflective relationship with the reflector portion 130 of lamp retainer 124. A lamp 132 useful with the laryngoscope 10 of the present invention is commercially available from Boehm under model no. X02.88.044.

Figure 7:
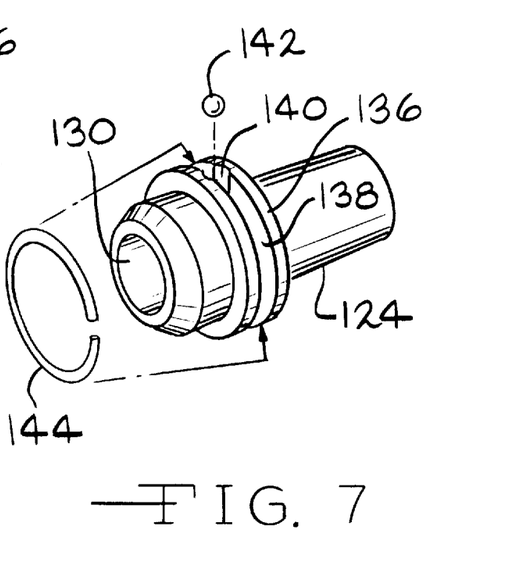
FIG. 7 is a perspective, exploded view of the lamp retainer 124 for the laryngoscope 10.

Lamp retainer 124 is provided with an annular enlarged portion 136 opposite a portion of the interior cylindrically-shaped bore 126 and adjacent to shoulder 128. An annular groove 138 in the enlarged portion 136 intersects an opening 140 communicating with the interior bore 126. A stainless steel detent in the shape of a ball 142 serving as a lamp holder is disposed inside the opening 140. Opening 140 is somewhat less in diameter than that of the detent 142 so that a portion of the detent protrudes into the bore 126 contacting the lamp casing 134 of lamp 132 received inside the bore 126. The detent 142 is retained in this position by a beryllium copper spring clip 144 seated in groove 146 in the annular enlarged portion 136 to thereby removably hold or retain the lamp 132 in the lamp retainer 124.

The lamp retainer 124 is itself secured in the internal bore 106 of head 100 by a lamp retainer ring 148 having exterior threads 150 that threadingly mate with the internal threaded portion 112 of head 100. The lamp retainer ring 148 is preferably constructed of chrome plated brass and further comprises an internal shoulder 152 meeting with an opening 154 that is only somewhat greater in diameter than the outer cylindrical side wall of the lamp retainer 124. With the lamp retainer 124 received in the internal bore 106 of head 100, a head spring 156, preferably constructed of silver plated beryllium copper and sized to surround the outer side wall of the lamp retainer 124, biases between the annular enlarged portion 136 of lamp retainer 124 and the shoulder portion 152 of the lamp retainer ring 148 threaded into the head 100.

The lamp 132 is provided with a contact 158 that extends beyond the retainer ring 148 and into the beveled portion 108 of head 100 with the external threads 24 of the cap portion 102 mated to the internal threads 24 at the proximal handle section 22. In this position, a shoulder 160 intermediate the external threads 104 and an annular step 162 abuts the end of the proximal handle section 22. An elastomeric O-ring 164 is received in the steps 162, held tightly between the cap 102 and handle 12.

Figure 6:
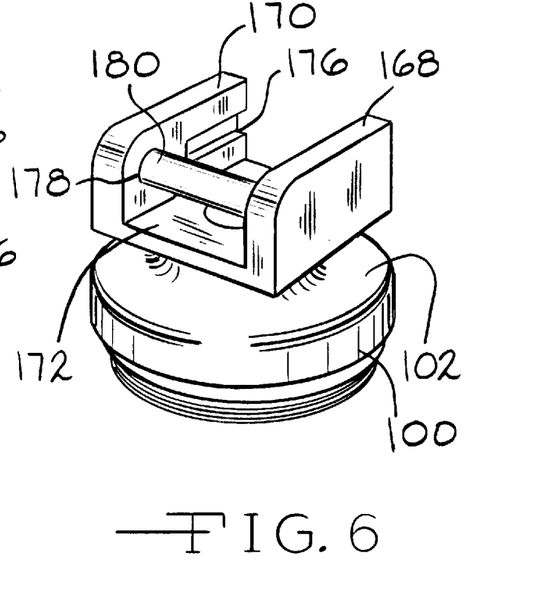
FIG. 6 is a perspective view of the head 100 for the laryngoscope 10.

The blade 14 is attached to the handle 12 in a pivotal manner by the attachment means 16 which includes a base portion 166 of blade 14, and a pair of opposed side walls 168 and 170 extending from a base plate 172 supported on the cap portion 102 of head 100. The side walls 168, 170 are provided with respective channels 174, 176 that extend part way across the length of the side walls from an end thereof. Each side wall 168, 170 further includes an opening 178 opposite the terminal end of the channels 174, 176.

The base portion 166 of the blade 14 is sized to be received between the side walls 168, 170 of head 100. The base portion 166 also has a through bore (not shown) sized to receive a pin 180, preferably constructed of stainless steel, and a pair of spring biased detents 182 (one shown in dashed lines in FIG. 1) that are receivable in the respective channels 174, 176.

To fix the blade 14 with respect to the handle 12 in the generally L-shaped configuration, the base portion 166 of blade 14 is positioned between the side walls 168, 170 of head 100 with the through bore aligned with the openings 178. The pin 180 is moved through the openings 178 and bore to thereby pivotably attach the blade 14 to the handle 12.

FIG. 3A shows that when the head 100 is threaded onto the proximal handle section 22, the contact 158 of lamp 132 contacts the proximal end 90 of the battery pin 62. The opposite, distal end 166 of the battery pin 62 is in a raised position, out of contact with the central, positive terminal 38 of battery 32. The lamp 132 is energized by pivoting the blade 14 with respect to the handle 12 about the pin 180 until the spring biased detents 182 seat in the opposed channels 174, 176 in side walls 168, 170. This movement serves to releasibly lock the blade 14 in the generally L-shaped configuration with respect to the handle 12. As the blade 14 is so pivoted, the base portion 166 contacts the lamp retainer 124, moving it and the lamp 132 towards the battery 32 and against the biasing force of head spring 156. The lamp contact 158 in turn forces the battery pin 62 towards the battery 32 against the biasing force of the battery spring 64 until the distal end 166 of the pin 62 contacts the central, positive terminal 38 of battery 32 (as shown in dashed lines in FIG. 3A). The electrical circuit is completed through the annular, negative contact ring 36, the spring contacts 68, the handle 12, the head 100, lamp retainer ring 148 and the detent 142 contacting the lamp casing 134. With the lamp 132 energized, light is directed to the blade light conductor 123 which transmits the light to the end of the blade 14. When the laryngoscope 10 is utilized during a medical examination or during the insertion of an endotracheal tube, the conductor 123 helps to illuminate the zone of interest to thereby aid the physician.

When the blade 14 is pivoted about pin 180 in the opposite direction to break the L-shaped configuration, the head spring 156 biases the lamp retainer 124 and lamp 132 away from the battery 32 and the battery spring 64 biases the battery pin 62 out of contact with the central, positive battery terminal 38.

In addition to serving as a portion of the electrical contact path for energizing the lamp 132, the lamp assembly 34 including the lamp retainer 126, detent 142 and spring clip 144 provide a structure for quickly and easily replacing the lamp 132 should it burn out or otherwise malfunction. To change the lamp 132, the head 100 is unscrewed from the proximal handle section 22 and the lamp retainer ring 150 is unthreaded from the head 100. This releases the lamp assembly 34 from the head 100 and the lamp 132 is easily moved out of the bore 126 in the lamp retainer 124, releasing from contact with the spring clip 144 biased detent 142. A new lamp 132 is then replaced inside the lamp retainer 124 and the lamp assembly 34 including spring 156 and lamp retainer ring 150 are then re-assembled inside the head 100 and the head is screwed onto the handle 12.

In accordance with the stated low magnetic susceptibility characteristics of the laryngoscope of the present invention, Table 1 lists the magnetic susceptibilities of the various materials used to construct the laryngoscope along with selected other materials.

TABLE 1

| Material | Density (g/cc) | Atomic or Molecular Weight | Susceptibility ($\times 10^6$) |
| --- | --- | --- | --- |
| Carbon (polycrystalline graphite) | 2.26 | 12.011 | −218 |
| Gold | 19.32 | 196.97 | −34 |
| Beryllium | 1.85 | 9.012 | −24 |
| Silver | 10.50 | 107.87 | −24 |
| Carbon (diamond) | 3.513 | 12.011 | −21.8 |
| Zinc | 7.13 | 65.39 | −15.7 |
| Copper | 8.92 | 63.546 | −9.63 |

TABLE 1-continued

| Material | Density (g/cc) | Atomic or Molecular Weight | Susceptibility (×10⁶) |
|---|---|---|---|
| Water (37° C.) | 1.00 | 18.015 | −9.03 |
| Human Soft Tissues | ~1.00–1.05 | — | ~(−11.0 to −7.0) |
| Air (NTP) | 0.00129 | 28.97 | +0.36 |
| Stainless Steel (nonmagnetic, austenitic) | 8.0 | — | 3520–6700 |
| Chromium | 7.19 | 51.996 | 320 |

It is known that brass is an alloy of copper and zinc.

In contrast, Table 2 lists the magnetic susceptibilities of various relatively highly magnetic materials.

TABLE 2

| Material | Density (g/cc) | Atomic or Molecular Weight | Susceptibility |
|---|---|---|---|
| Nickel | 8.9 | 58.69 | 600 |
| Stainless Steel (magnetic, martensitic) | 7.8 | — | 400–1100 |
| Iron | 7.874 | 55.847 | 200,000 |

The data use to construct Tables 1 and 2 was obtained from a paper authored by John Schneck of General Electric Corporate Research and Development Center, Schenectady, N.Y. 12309, entitled "The Role of Magnetic Susceptibility In Magnetic Resonance Imaging:Magnetic Field Compatibility of the First and Second Kinds". The disclosure of that paper is incorporated herein by reference.

Thus, the laryngoscope of the present invention is an instrument which is useful for pre and post clinical and surgical applications, especially in an environment proximate the strong magnetic field emitted by a magnetic resonance scanner.

It is appreciated that various modifications to the inventive concepts described herein may be apparent to those of ordinary skill in the art without departing from the spirit and scope of the present invention as defined by the appended claims.

What is claimed is:

1. A laryngoscope, which comprises:

a) a handle;

b) an attachment means provided at an end of the handle, wherein the attachment means provides for detachably mounting a laryngoscope blade thereon;

c) a lamp means housed inside the handle as a light source for directing light towards the blade; and d) a battery housed inside the handle to electrically energize the lamp means, wherein the battery has a first end facing the lamp means and a second end, and wherein the second end and at least part of the battery side wall between the ends are provided with an insulative material to prevent electrical contact therewith, and wherein the first end of the battery comprises a first, continuous terminal surrounding a second terminal such that with the laryngoscope blade unattached to the attachment means, the lamp means is in an unenergized state and with the blade attached to the attachment means in an operative position, the lamp means is caused to move inside the handle to make electrical contact with the second terminal to thereby complete an electrical path that energizes the lamp directing light towards the blade.

2. The laryngoscope of claim 1 wherein the first, continuous terminal of the battery is in the shape of a ring at the first end of the battery.

3. The laryngoscope of claim 1 wherein the second terminal of the battery is centered along a longitudinal axis of the battery.

4. The laryngoscope of claim 1 wherein the first, continuous terminal of the battery comprises a ring at the first end and the second terminal is disposed in a recessed position towards the second end of the battery with respect to a plane of the ring.

5. The laryngoscope of claim 1 wherein the battery is an alkali metal battery.

6. The laryngoscope of claim 1 wherein the battery is a lithium/thionyl chloride-bromine chloride battery.

7. A laryngoscope, which comprises:

a) a handle;

b) an attachment means provided at an end of the handle, wherein the attachment means provides for detachably mounting a laryngoscope blade thereon;

c) a lamp means housed inside the handle as a light source for directing light towards the blade; and d) a battery housed inside the handle to electrically energize the lamp means, wherein the lamp means comprises a lamp retainer having a retainer side wall provided with a bore for receiving a lamp therein and wherein the retainer side wall has an opening communicating with the bore and adapted to receive a spring biased detent contacting a side wall of the lamp such that the lamp is held in the bore by the spring biased detent during operation of the laryngoscope and wherein the lamp is released from the retainer by movement of the lamp through the bore against the force of the spring biased detent for replacing the lamp.

8. The laryngoscope of claim 7 wherein the retainer side wall mounts a spring clip that biases the detent towards the bore.

9. The laryngoscope of claim 7 wherein the detent is a ball.

10. A laryngoscope, which comprises:

a) a handle;

b) an attachment means provided at an end of the handle, wherein the attachment means provides for detachably mounting a laryngoscope blade thereon;

c) a lamp means housed inside the handle as a light source for directing light towards the blade; and d) a battery housed inside the handle to electrically energize the lamp means, wherein the battery has a first end facing the lamp means and a second end and wherein the second end and at least part of the battery side wall between the ends are provided with an insulative material to prevent electrical contact therewith, and wherein the first end of the battery comprises a first, continuous terminal surrounding a second terminal such that with the laryngoscope blade unattached to the attachment means, the lamp means is in an unenergized state and with the blade attached to the attachment means in an operative position, the lamp means is caused to move inside the handle to make electrical contact with the second terminal to thereby complete an electrical path that energize the lamp directing light towards the blade and wherein the lamp means comprises a lamp retainer having a retainer side wall provided with a bore for receiving a lamp therein and wherein the retainer side wall has an opening communicating with the bore and adapted to receive a spring biased detent contacting a side wall of the lamp such that the lamp is held in the bore by the spring biased detent during operation of the laryngoscope and wherein the lamp is released from the retainer by movement of the lamp through the bore against the force of the spring biased detent for replacing the lamp.

11. The laryngoscope of claim 10 wherein the first, continuous terminal of the battery comprises a ring at the first end and the second terminal is disposed in a recessed position towards the second end of the battery with respect to a plane of the ring.

12. The laryngoscope of claim 10 wherein the retainer side wall mounts a spring clip that biases the detent towards the bore.

13. A laryngoscope, which comprises:
  a) a handle;
  b) an attachment means provided at an end of the handle, wherein the attachment means provides for detachably mounting a laryngoscope blade thereon;
  c) a lamp means housed inside the handle as a light source for directing light towards the blade; and
  d) a battery provided inside the handle to electrically energize the lamp means, wherein the battery is an alkali metal battery housed inside of an austenitic stainless steel casing having a magnetic susceptibility of about $6,700 \times 10^6$ or less and wherein the internal electrical battery components, the handle, the attachment means and the lamp means have magnetic susceptibilities at least as low as that of austenitic stainless steel.

14. The laryngoscope of claim 13 wherein the handle is of chrome plated brass.

15. The laryngoscope of claim 13 wherein the attachment means is of chrome plated brass and stainless steel.

16. The laryngoscope of claim 13 wherein lamp means is of stainless steel and beryllium copper.

17. A method of assembling a laryngoscope, comprising the steps of:
  a) providing a handle having an attachment means at an end thereof, wherein the attachment means provides for detachably mounting a laryngoscope blade thereon;
  b) housing a lamp means inside the handle as a light source for directing light towards the blade;
  c) providing a battery inside the handle to electrically energize the lamp means, wherein the battery has a first end facing the lamp means and a second end and wherein the second end and at least part of the battery side wall between the ends are provided with an insulative material to prevent electrical contact therewith, and wherein the first end of the battery comprises a first, continuous terminal surrounding a second terminal; and
  d) attaching the laryngoscope blade to the attachment means in an operative position causing the lamp means to move inside the handle to make electrical contact with the second terminal to thereby complete an electrical path that energize the lamp directing light towards the blade, and wherein when the laryngoscope blade is detached from the attachment means, the lamp means moves to out of contact with the battery.

18. The method of claim 17 including providing the first, continuous terminal of the battery in the shape of a ring at the first end of the battery.

19. The method of claim 17 including providing the second terminal of the battery centered along a longitudinal axis of the battery.

20. The method of claim 17 including providing the first, continuous terminal of the battery comprising a ring at the first end and the second terminal disposed in a recessed position towards the second end of the battery with respect to a plane of the ring.

21. The method of claim 17 including providing the battery as an alkali metal battery.

22. A method of assembling a laryngoscope, comprising the steps of:
  a) providing a handle having an attachment means at an end thereof, wherein the attachment means provides for detachably mounting a laryngoscope blade thereon;
  b) housing a lamp means inside the handle as a light source for directing light towards the blade, wherein the lamp means comprises a lamp retainer having a retainer side wall provided with a bore for receiving a lamp therein and wherein the retainer side wall has an opening communicating with the bore and adapted to receive a spring biased detent contacting a side wall of the lamp such that the lamp is held in the bore by the spring biased detent during operation of the laryngoscope;
  c) providing a battery inside the handle to electrically energize the lamp means and;
  d) releasing the lamp from the retainer by movement of the lamp through the bore against the force of the spring biased detent at such time as the lamp requires replacing.

23. The method of claim 22 including providing the retainer side wall mounting a spring clip that biases the detent towards the bore.

24. The method of claim 22 including providing the detent as a ball.

25. A method of assembling a laryngoscope, comprising the steps of:
  a) providing a handle having an attachment means at an end thereof, wherein the attachment means provides for detachably mounting a laryngoscope blade thereon;
  b) housing a lamp means inside the handle as a light source for directing light towards the blade; and
  c) providing a battery housed inside the handle to electrically energize the lamp means including providing the battery as an alkali metal battery housed inside of an austenitic stainless steel casing having a magnetic susceptibility of about $6,700 \times 10^6$ or less and further providing the internal electrical battery components, the handle, the attachment means and the lamp means having magnetic susceptibilities at least as low as that of austenitic stainless steel.

26. The method of claim 25 including the handle of chrome plated brass.

27. The method of claim 25 including providing the attachment means of chrome plated brass and stainless steel.

28. The method of claim 25 including providing the lamp means of stainless steel and beryllium copper.

* * * * *